United States Patent [19]

Wilson

[11] Patent Number: 4,575,454
[45] Date of Patent: Mar. 11, 1986

[54] METAL ION CONTROL AGENTS BASED ON DICYCLOPENTADIENE DERIVATIVES

[75] Inventor: David A. Wilson, Richwood, Tex.

[73] Assignee: The Dow Chemical Company, Midland, Mich.

[21] Appl. No.: 612,109

[22] Filed: May 21, 1984

Related U.S. Application Data

[62] Division of Ser. No. 486,122, Apr. 18, 1983, Pat. No. 4,500,470.

[51] Int. Cl.$^4$ .................. C02F 5/12; C02B 5/06; C01G 1/00
[52] U.S. Cl. .................. 423/139; 75/101 BE; 210/699; 210/700; 210/688; 423/21.5; 423/24; 423/54; 423/63; 423/70; 423/100; 423/112; 423/157; 423/181; 423/658.5; 423/DIG. 14
[58] Field of Search .............. 423/659, DIG. 14, 139, 423/157, 658.5; 75/101 BE; 210/687, 688, 698, 699, 700; 260/502 E, 503; 562/499; 252/180

[56] References Cited

U.S. PATENT DOCUMENTS

| | | | |
|---|---|---|---|
| 2,599,807 | 6/1952 | Bersworth | 260/500 |
| 2,609,390 | 9/1952 | Bersworth | 260/500 |
| 3,288,846 | 11/1966 | Irani et al. | 260/500 |
| 3,331,773 | 7/1967 | Gunderson et al. | 210/58 |
| 3,336,721 | 8/1967 | Ralston | 210/58 |
| 3,434,969 | 3/1969 | Ralston | 210/58 |
| 3,674,804 | 7/1972 | Redmore | 260/309.6 |
| 3,720,498 | 3/1973 | Redmore | 21/2.5 |
| 3,743,603 | 7/1973 | Redmore | 252/180 |
| 3,859,211 | 1/1975 | Redmore | 210/54 |
| 3,954,761 | 5/1976 | Redmore | 260/268 K |
| 4,051,110 | 9/1977 | Quinlan | 260/72 R |
| 4,229,294 | 10/1980 | Redmore et al. | 210/700 |
| 4,307,038 | 12/1981 | Sommer et al. | 260/520.5 E |
| 4,323,461 | 4/1982 | Quinlan | 210/700 |
| 4,330,487 | 5/1982 | Redmore et al. | 210/700 |
| 4,416,785 | 11/1983 | Redmore et al. | 210/699 |

OTHER PUBLICATIONS

Proc. Int. Water Con. Eng. Soc., West Pa, 41 pp. 167–174, "Toward a Better Understanding of Commercial Organophosphonates, Roderick A. Campbell.
Townsend, Jeffery A. et al., Proc. Int. Water Conf. Soc., West Pa., pp. 89–99, 1978, Scaled Deposit Control in Cooling Water Systems.
Hoest, Organic Chemical Brochure, title page & pp. 4, 14 & 15.

Primary Examiner—Gary P. Straub
Attorney, Agent, or Firm—A. C. Ancona

[57] ABSTRACT

New compounds have been prepared from dicyclopentadiene bis(methylamine) which have the following formula

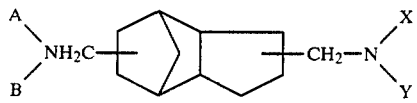

wherein substituents A, B, X and Y each are independently selected from radicals including hydrogen, hydroxyalkyl (wherein the alkyl group contains 2-6 carbon atoms) phosphonic, sulfonic, hydroxyethyl- and hydroxypropylsulfonic, methylenephosphonic methylene-, ethylene- and propylenesulfonic, alkylcarboxylic acid radicals (having 2-4 carbon atoms) and the alkali or alkaline earth metal, ammonia and amine salts of any of the phosphonic, sulfonic or carboxylic acid derivatives. At least one of the substituents must be other than a hydrogen. These compounds are useful chelating agents and those containing the methylenephosphonic substituents are good threshold agents.

9 Claims, No Drawings

METAL ION CONTROL AGENTS BASED ON DICYCLOPENTADIENE DERIVATIVES

This is a divisional of application Ser. No. 486,122, filed Apr. 18, 1983, now U.S. Pat. No. 4,500,470.

BACKGROUND OF THE INVENTION

Dicyclopentadiene (DCPD) is a relatively plentiful diunsaturated monomer with a variety of potential uses due to the ease of making derivatives by reaction with the double bonds. Its source is the bottoms of light hydrocarbon distillation columns wherein it is formed by prolonged heating of the $C_5$ fraction. It has the following structure

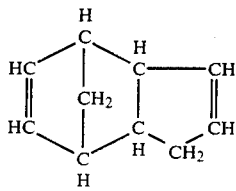

Reactions are known to form the nitrile or dinitrile by reacting the double bonds of DCPD with HCH; the nitrile can then be hydrolyzed to form the carboxylic acid derivative. The DCPD can also be catalytically reacted with HCN, followed by reduction to obtain the bis methylamine derivative; this product in turn can be reacted with glycolonitrile in the presence of caustic to give the sodium salt of tetraacetic acid of the bis amine, a likely chelating agent since it resembles EDTA.

It is well known that amines such as ethylenediamine and diethylenetriamine can be reacted with formaldehyde and phosphorus acid to obtain methylene phosphonate derivatives of the amine in which the methylene phosphonate group

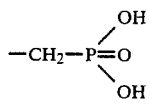

substitutes for the amine hydrogens (U.S. Pat. No. 3,288,846).

The use of methylenephosphonic acid substituted alkylene polyamines for metal ion control at less than stoichiometric amounts was suggested in a patent (U.S. Pat. No. 2,609,390) issued in 1952. Later a water dispersible polymeric amine chelating agent which included alkylene phosphonate derivatives was indicated as having "threshold" effects in scale inhibition applications (see U.S. Pat. No. 3,331,773), this term being used to describe the use of the agent in less than stoichiometric amounts. The diamine and polyamine methylenephosphonate derivatives are taught and claimed in U.S. Pat. Nos. 3,336,221 and 3,434,969, respectively. Some of the products disclosed in these two patents are available commercially and are recommended as scale inhibitors when applied in threshold amounts.

Other patents which disclose heterocyclic nitrogen containing compounds which are useful as chelating agents and may be employed in threshold amounts are U.S. Pat. Nos. 3,674,804; 3,720,498; 3,743,603; 3,859,211; and 3,954,761. Some of the compounds included therein are heterocyclic compounds having the formulas:

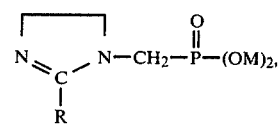

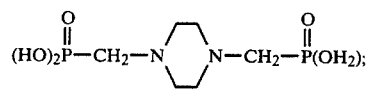

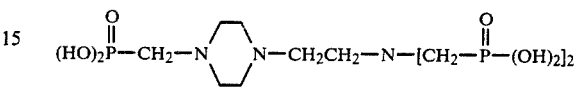

and

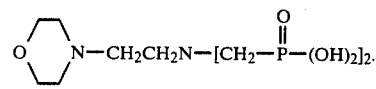

wherein R is hydrogen or alkyl and M is hydrogen, alkali metal, ammonium or a di- or triethanolamine radical;

Methylenephosphonates of polyalkylene polyamines, disclosed in U.S. Pat. No. 4,051,110, are made by reacting di- or polyamines with a chain extending agent such as a dihalide or an epoxyhalide, e.g. ethylene dichloride or epichlorohydrin and thereafter, with phosphorus acid and formaldehyde. Thus, for example, triethylenetetramine is reacted with epichlorohydrin in an approximately one to one mole ratio; thereafter the product is reacted with phosphorus acid, and formaldehyde in the presence of hydrochloric acid. The resulting methylenephosphonated polyamine is useful in small amounts as a scale inhibitor, being employed at concentrations of 20–50 ppm.

Certain phosphonic acid derivatives of the aliphatic acids can be prepared by reacting phosphorus acid with acid anhydrides or acid chlorides, e.g. the anhydrides or chlorides of acetic, propionic and valeric acids. The compounds prepared have the formula

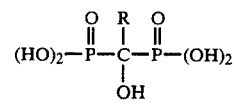

wherein R is a lower alkyl radical having 1 to 5 carbon atoms. The method of making and use of these products is described in U.S. Pat. No. 3,214,454. The use of threshold amounts to prevent calcium precipitation is disclosed and claimed therein.

It has now been discovered that new chelating and threshold agents for inhibiting precipitation of metal ions can be made from the bis(methylamine) derivatives of dicyclopentadiene. They can also be considered as tricyclodecane derivatives. Thus, dicyclopentadiene bis(methylamine) can be named 3(4), 8(9)-bis(aminomethyl)-tricyclo[5.2.1.0$^{2,6}$]decane.

SUMMARY OF THE INVENTION

A new class of compounds is formed when dicyclopentadiene bis(methylamine) is reacted with certain compounds, e.g. formaldehyde and phosphorous acid will form methylenephosphonic acid derivatives. These new compounds have the structure

wherein substituents A, B, X and Y each are independently selected from radicals including hydrogen, hydroxyalkyl (wherein the alkyl group contains 2-6 carbon atoms) phosphonic, sulfonic, methylenephosphonic, methylene-, ethylene- and propylene-sulfonic, carboxylic acid radicals (having 2-4 carbon atoms) and the alkali or alkaline earth metal, ammonia and amine salts of any of the phosphonic, sulfonic or carboxylic acid derivatives. At least one of the substituents must be other than a hydrogen.

DETAILED DESCRIPTION OF THE INVENTION

When formaldehyde and phosphorus acid are reacted with DCPD bis(methylamine), hereinafter DCPD-BMA, the result in a new compound having the following structure:

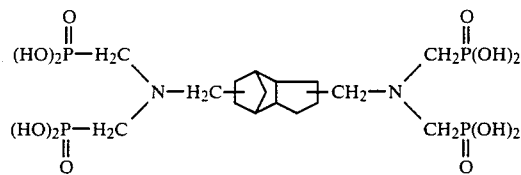

The above compound has been found to have excellent threshold properties.

Other substituents for the hydrogens of the amine groups of the above DCPD derivatives form useful chelating agents, but only the methylenephosphonic acid substituted compounds and their alkali, alkaline earth metal, ammonia or amine salt derivatives are effective as threshold agents.

Substituents other than methylenephosphonates give compounds having the following structure:

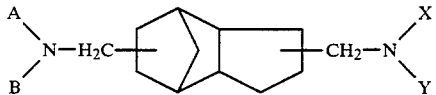

wherein A, B, X, Y can be hydrogen, hydroxyalkyl, wherein the alkyl group contains 2 to 6 carbon atoms, hydroxyethyl- and hydroxypropylsulfonic, phosphonic, sulfonic, methylene-, ethylene- and propylenesulfonic, alkylcarboxylic acid radicals, and their alkali or alkaline earth metal, ammonia or amine salts, with the proviso that at least one of the groups must be other than hydrogen.

The following examples illustrate the preparation of the new compounds.

EXAMPLE 1

Deionized water (100 g) and 49.0 g (0.25 mole) of DCPD-BMA weighed into a 500 ml round-bottom reaction flask equipped with a water-cooled reflux condenser, mechanical stirrer, thermometer with a temperature controller, and an addition funnel. Approximately 120 g of concentrated HCl solution and 98.7 g (1.20 mole) of phosphorous acid were added to the aqueous amine solution and the reaction mixture heated to reflux and maintained for one hour. Aqueous 37% formaldehyde solution (85.1 g, 1.05 mole) was added to the addition funnel and added over a two hour period. The reaction mixture was heated at reflux for an additional two hours and then cooled. The product obtained was the DCPD-BMA derivative in which each amine hydrogen is replaced by a methylenephosphonic acid group

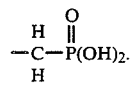

EXAMPLE 2

The procedure of Example 1 was followed except 0.60 mole of phosphorous acid and 0.53 mole of aqueous formaldehyde solution were used. The product obtained was the DCPD-BMA derivative in which there are two methylenephosphonic acid group substituents with two hydrogens remaining unsubstituted.

EXAMPLE 3

The procedure of Example 2 was repeated and the reaction product carboxymethylated using 0.55 mole of aqueous glycolonitrile (HOCH$_2$C≡N) in the presence of excess caustic to produce the sodium salt of the aminocarboxylic acid. The product obtained was the DCPD-BMA derivative containing two methylene sodium phosphonate and two sodium acetate groups.

EXAMPLE 4

Deionized water (40 g) and 24.5 g (0.125 mole) of DCPD-BMA were weighed into a 500 ml round-bottom flask equipped with a water-cooled reflux condenser, mechanical stirrer, thermometer with a temperature controller, and an addition funnel. Caustic solution (10.1 g of 50%) and 25.0 g (0.127 mole) the sodium salt of 3-chloro-2-hydroxy-1-propanesulfonic acid, were added with stirring and the reaction mixture heated at 85° C. for one hour. Additional caustic solution (12.0 g of 50%) and 25.0 g of the sodium salt of 3-chloro-2-hydroxy-1-propanesulfonic acid, were then added and the solution heated at 85° C. for 1½ hours. Approximately 60 g of concentrated HCl solution and 24.7 g (0.300 mole) of phosphorous acid were added and the reaction mixture heated to reflux and maintained for one hour. Aqueous 37% formaldehyde solution (21.3 g, 0.263 mole) was added to the addition funnel and added over about a one-hour period. The reaction mixture was heated at reflux for an additional three hours and then cooled. The product obtained was the DCPD-BMA derivative containing two methylenephosphonic acid and two 2-hydroxypropylsulfonic acid and two 2-hydroxypropylsulfonic acid groups —H$_2$C-CHOH-CH$_2$-SO$_3$H.

EXAMPLE 5

The procedure of Example 4 was followed except 0.127 mole of the sodium salt of 3-chloro-2-hydroxy-1-propanesulfonic acid, 37.0 g (0.350 mole) of phosphorus acid, and 32.0 g (0.3944 mole) of 37% formaldehyde solution were used. The product obtained was the DCPD-BMA derivative containing three methylenephosphonic acid groups and one 2-hydroxypropylsulfonic acid group.

EXAMPLE 6

Deionized water (40 g) and 24.5 g (0.125 mole) of DCPD-BMA were weighed into a 500 ml round-bottom reaction flask equipped with a water-cooled reflux condenser, mechanical stirrer, thermometer with a temperature controller, and an addition funnel. Caustic solution (10.1 g of 50%) and 25.0 g (0.127 mole) of the sodium salt of 3-chloro-2-hydroxyl-1-propanesulfonic acid, were then added and heating continued for one hour at 85° C. The addition of caustic solution and of the sodium salt 3-chloro-2-hydroxy-1-propanesulfonic acid, was repeated three more times as outlined above except that the reaction solution was maintained at 85° C. for two hours after each addition. The product obtained was the DCPD-BMA derivative containing four 2-hydroxypropyl sodium sulfonate groups, i.e. all amine hydrogens were substituted with that same group.

EXAMPLE 7

Ethylene oxide (11.6 g, 0.263 mole) was reacted with 24.5 g (0.125 mole) of DCPD-BMA and the reaction product then phosphonomethylated according to the procedure of Example 1 using 0.300 mole of phosphorous acid and 0.263 mole of formaldehyde solution. The product obtained was the DCPD-BMA derivative containing two hydroxyethyl and two methylenephosphonic acid groups.

EXAMPLE 8

The procedure of Example 7 was followed except that amine was reacted with 0.132 mole of ethylene oxide and the reaction product phosphonomethylated using 0.450 mole of phosphorous acid and 0.394 mole of formaldehyde solution. The product obtained was the DCPD-BMA derivative containing one hydroxyethyl group and three methylenephosphonic acid groups.

EXAMPLE 9

Propylene oxide (7.6 g, 0.130 mole) was reacted with 24.5 g (0.125 mole) of DCPD-BMA and the reaction product then phosphonomethylated according to the procedure of Example 1 using 0.450 mole of phosphorous acid and 0.394 mole of formaldehyde solution. The product obtained was the same as that of Example 8 except for a hydroxypropyl group in place of the hydroxyethyl group.

EXAMPLE 10

Sodium bisulfite (13.7 g, 0.131 mole) and 15 g of distilled water were added to a round-bottom reaction flask equipped with a water-cooled reflux condenser, mechanical stirrer, thermometer with a temperature controller, and an addition funnel. Formaldehyde solution (10.7 g of 37% 0.131 mole) was added to the addition funnel and added with stirring to the sodium bisulfite-water mix over a 5-minute period. The reaction product was then heated to 75° C. for one-half hour and then cooled. The sodium bisulfite-formaldehyde reaction solution was transferred to the addition funnel and 24.5 g (0.125 mole) of DCPD-BMA and 20 g of distilled water added to the reaction flask. The amine solution was heated to 75° C. and the sodium bisulfite-formaldehyde solution added over a one-hour period and then heated at 75° C. for three hours. Concentrated HCl (75 g) and 37 g (0.450 mole) of phosphorous acid were added to the flask and the mixture heated to 100° C. Formaldehyde solution (32.0 g, 0.394 mole) was added to the addition funnel and added over a 20-minute period. The reaction mixture was heated at 100° C. for 40 minutes and then at reflux for an additional three hours before cooling. The product obtained was the DCPD-BMA derivative containing one methylenesulfonic acid group and three methylenephosphonic acid groups.

It should be recognized that when mixed derivatives are obtained, it is not usually possible to direct or predict which amine hydrogens are substituted. The product, in all probability, contains a mixture of isomeric compounds.

To show the usefulness of the compounds of the present invention, the following test was run to determine calcium scale inhibition:

Several 50 ml samples of a 0.02M $CaCl_2$ solution were placed in 4-oz. bottles. To these solutions was added the candidate inhibitor in various concentrations. Fifty-ml samples of a 0.04M sodium bicarbonate/0.96M sodium chloride solution were then added with stirring. A total hardness determination was made on the mixture by adding excess standard EDTA and back titrating with standard $Mg^{++}$ solution in the presence of Eriochrome Black T indicator. The samples were placed in an 80° C. oven and 10-ml samples taken periodically from each bottle, filtered through a millipore filter, and the total hardness of the filtrates determined by titration. A blank with no inhibitor was run in an identical manner. The percent inhibition was calculated from the total hardness before heating and the total hardness found after heating at 80° C. for 24 hours.

Table I shows results obtained with the compounds of the present invention compared to two of the more widely used commercially available organophosphonate scale inhibitors.

TABLE I

| Scale Inhibition Data | | |
| --- | --- | --- |
| Compound Used | Concentration* | % Inhibition |
| None | — | 7.2 |
| Example 1 | 10 ppm | 43.4 |
| Example 2 | 10 ppm | 29.0 |
| Example 3 | 10 ppm | 35.5 |
| Example 4 | 10 ppm | 40.2 |
| Example 5 | 10 ppm | 39.0 |
| Example 6 | 10 ppm | 24.2 |
| Example 7 | 10 ppm | 27.7 |
| Example 8 | 10 ppm | 42.8 |
| Example 9 | 10 ppm | 43.8 |
| Example 10 | 10 ppm | 42.2 |
| Aminotri(methylenephosphonic acid) pentasodium salt | 10 ppm | 39.3 |
| 1-hydroxyethylidene-1,1-diphosphonic acid | 10 ppm | 40.3 |

*ppm based on active acid

The usefulness of the compounds of the present invention to act as chelating agents was demonstrated by preparing iron chelate solutions that were 0.01M in ferric iron. Fifty ml aliquots were taken and the pH adjusted with aqueous ammonia to approximately 7.5, 8.3, 9.0, and 10.0. The samples were allowed to stand for about two weeks and then soluble iron determined by analyzing the clear overhead. The data obtained for three of the compounds of the present invention is summarized in Table II and compared with two commercially available chelating agents.

TABLE II

| Chelant Used | Molar Concn. | Percent of Total Iron Remaining in Solution at pH | | | |
|---|---|---|---|---|---|
| | | 7.5 | 8.3 | 9.0 | 10.0 |
| None | — | <1.0 | <1.0 | <0.5 | <0.2 |
| Example 1 | 0.01 | 100 | 91.1 | 100 | 100 |
| Example 5 | 0.01 | 71.0 | 91.0 | 100 | 14.4 |
| Example 8 | 0.01 | 78.6 | 87.5 | 87.5 | 92.9 |
| Glycolic acid | 0.04 | 96.2 | <0.2 | <0.2 | <0.2 |
| Glycolic acid | 0.10 | 96.2 | 96.2 | <0.5 | <0.2 |
| Glycolic acid | 0.20 | 94.3 | 96.2 | 24.5 | <0.5 |
| HEIDA* | 0.01 | 100 | 100 | 100 | 28.3 |

*HEIDA = N—hydroxyethyliminodiacetic acid

I claim:

1. A process for inhibiting the precipitation of alkaline earth metal ions from their aqueous solutions which comprises adding to said solutions in less than stoichiometric amounts, based on the metal ions present, a compound of the formula

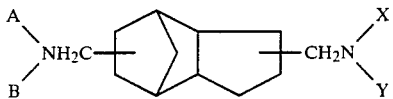

wherein substituents A, B, X and Y are each independently selected from radicals including hydrogen, hydroxyalkyl (wherein the alkyl group contains 2-6 carbon atoms) phosphonic, sulfonic, hydroxyethyl- and hydroxypropylsulfonic methylenephosphonic, methylene-, ethylene- and propylenesulfonic, alkylcarboxylic acid radicals (having 2-4 carbon atoms) and the alkali or alkaline earth metal, ammonia and amine salts thereof and wherein at least one of said substituents is a methylenephosphonic acid radical or a salt thereof.

2. The process of claim 1 wherein the substituent salt of the methylenephosphonic acid radical is an alkali metal salt.

3. The process of claim 1 wherein the substituent salt of the methylenephosphonic acid is an amine salt.

4. The process of claim 1 wherein the substituent salt of the methylenephosphonic acid is an alkaline earth metal salt.

5. The process of claim 4 wherein the alkaline earth metal is magnesium, calcium or barium.

6. The process of claim 1 wherein the substituent salt of the methylenephosphonic acid is an ammonium salt.

7. A process for chelating metal ions in an aqueous solution thereof which comprises adding thereto at least a stoichiometric amount based on the metal ions present, of a compound, having the following formula

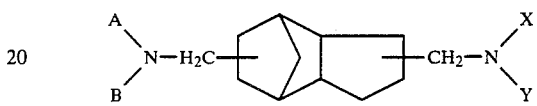

wherein substituents A, B, X and Y each are independently selected from radicals including hydrogen, hydroxyalkyl (wherein the alkyl group contains 2-6 carbon atoms) phosphonic, sulfonic, hydroxyethyl- and hydroxypropylsulfonic, methylenephosphonic, methylene-, ethylene- and propylenesulfonic, alkylcarboxylic acid radicals (having 2-4 carbon atoms) and the alkali or alkaline earth metal, ammonia and amine salts thereof and wherein at least one A, B, X and Y is other than hydrogen.

8. The process of claim 7 wherein A, B, X and Y are each methylenephosphonic acid radicals.

9. The process of claim 8 wherein the acid radicals are in a salt form.

* * * * *

UNITED STATES PATENT AND TRADEMARK OFFICE
CERTIFICATE OF CORRECTION

PATENT NO.  : 4,575,454
DATED       : March 11, 1986
INVENTOR(S) : David A. Wilson It is certified that error appears in the above-identified patent and that said Letters Patent is hereby corrected as shown below:

Col. 1, line 27, change "HCH;" to --HCN--.

Col. 3, line 24, change "in" to --is--.

Col. 4, lines 58 and 59, delete the second "and two 2-hydroxypropyl-sulfonic acid".

Col. 4, line 65, change "(0.350 mole)" to --(0.450 mole)--.

Col. 4, line 66, change "(0.3944 mole)" to --(0.394 mole)--.

Col. 5, line 11, change "-2-hydroxyl-1-" to -- -2-hydroxy-1- --.

Col. 5, line 34, change "that" to --the--.

Col. 5, line 57, insert a comma after "37%" and before "0.131".

Col. 7, line 32, Claim 1, insert a comma after "hydroxypropylsulfonic" and before "methylenephosphonic,".

Signed and Sealed this

Ninth Day of September 1986

[SEAL]

Attest:

DONALD J. QUIGG

Attesting Officer

Commissioner of Patents and Trademarks